US00PP37321P2

(12) United States Plant Patent
Sakazaki et al.

(10) Patent No.: US PP37,321 P2
(45) Date of Patent: Mar. 10, 2026

(54) ***PETUNIA* PLANT NAMED 'WNPETSVBG27'**

(50) Latin Name: *Petunia X hybrida*
Varietal Denomination: WNPETSVBG27

(71) Applicants: Ushio Sakazaki, Shiga (JP); Kevin A. Hurd, Austin, TX (US)

(72) Inventors: Ushio Sakazaki, Shiga (JP); Kevin A. Hurd, Austin, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 19/329,790

(22) Filed: Sep. 16, 2025

(51) Int. Cl.
*A01H 5/02* (2018.01)
*A01H 6/82* (2018.01)

(52) U.S. Cl.
USPC ..... Plt./356.21

(58) Field of Classification Search
USPC ..... Plt./356.1, 356.18, 356.19, 356.21
See application file for complete search history.

(56) References Cited

U.S. PATENT DOCUMENTS

PP34,152 P2 * 4/2022 Barnes ..... Plt./356.22

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct *Petunia* plant named 'WNPETSVBG27', characterized by its upright to outwardly spreading and mounding plant habit to spreading to trailing with subsequent development; vigorous growth habit and rapid growth rate; freely branching habit; dense and bushy plant form; medium green-colored leaves; early and freely flowering habit; uniform single-type flowers that are deep purplish pink in color; and good container and garden performance.

2 Drawing Sheets

Figure 1:
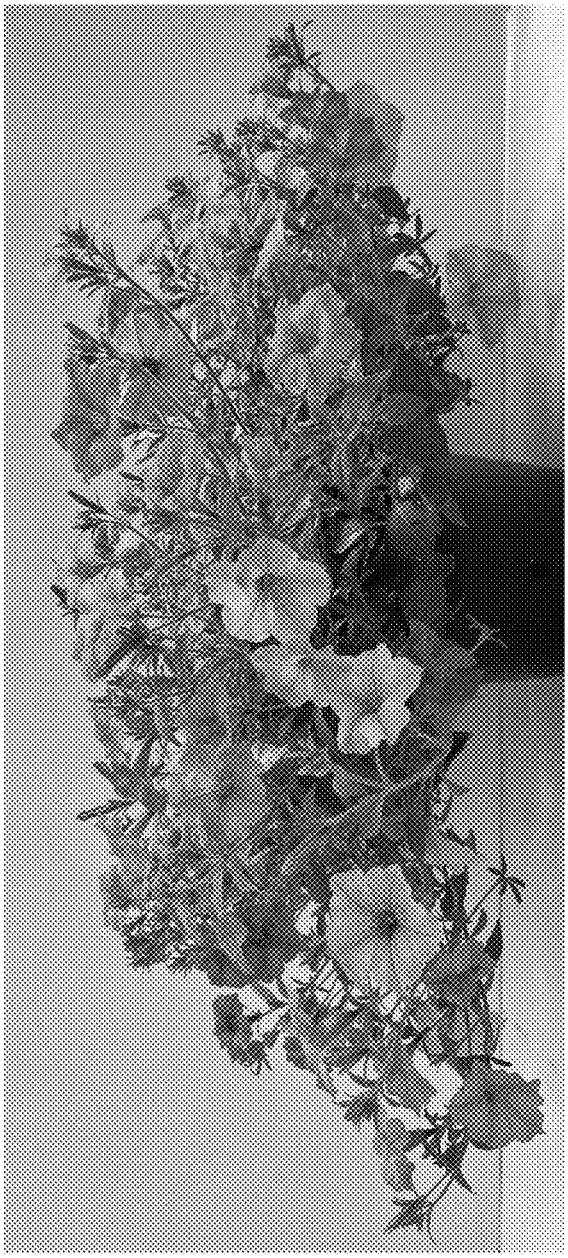

Botanical designation: *Petunia X hybrida.*
Cultivar denomination: 'WNPETSVBG27'.

BACKGROUND OF THE INVENTION

The present invention relates to a new and distinct cultivar of *Petunia* plant, botanically known as *Petunia* X *hybrida* and hereinafter referred to by the name 'WNPETSVBG27'.

The new *Petunia* plant is a naturally-occurring whole plant mutation of *Petunia* X *hybrida* 'USTUNI6001', disclosed in U.S. Plant Pat. No. 17,730. The new *Petunia* plant was discovered and selected by the Inventors as a single flowering plant from within a population of plants of 'USTUNI6001' in a controlled greenhouse environment in Carleton, Michigan on Oct. 23, 2024.

Asexual reproduction of the new *Petunia* plant by vegetative terminal cuttings in a controlled greenhouse environment in Carleton, Michigan since Oct. 24, 2024 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNPETSVBG27'. These characteristics in combination distinguish 'WNPETSVBG27' as a new and distinct *Petunia* plant:

1. Upright to outwardly spreading and mounding plant habit to spreading to trailing with subsequent development.
2. Vigorous growth habit and rapid growth rate.
3. Freely branching habit; dense and bushy plant form.
4. Medium green-colored leaves.
5. Early and freely flowering habit.
6. Uniform single-type flowers that are deep purplish pink in color.
7. Good container and garden performance.

Plants of the new *Petunia* can be compared to plants of the mutation parent, 'USTUNI6001'. In side-by-side comparisons, plants of the new *Petunia* differ primarily from plants of 'USTUNI6001' in the following characteristics:

1. Leaves of plants of the new *Petunia* are darker green in color than leaves of plants of 'USTUNI6001'.
2. Flower petals of plants of the new *Petunia* are deeper purplish pink in color than flower petals of plants of 'USTUNI6001'.

Plants of the new *Petunia* can be compared to plants of *Petunia* X *hybrida* 'WNPESVJAZ', disclosed in U.S. Plant Pat. No. 34,152. In side-by-side comparisons, plants of the new *Petunia* differ primarily from plants of 'WNPESVJAZ' in the following characteristics:

1. Plants of the new *Petunia* are more upright than and not as outwardly spreading as plants of 'WNPESVJAZ'.
2. Plants of the new *Petunia* have slightly larger flowers than plants of 'WNPESVJAZ'.

3. Flower petals of plants of the new *Petunia* are deep purplish pink in color whereas flower petals of plants of 'WNPESVJAZ' are reddish purple in color.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'WNPETSVBG27' grown in a container.

Figure 2:
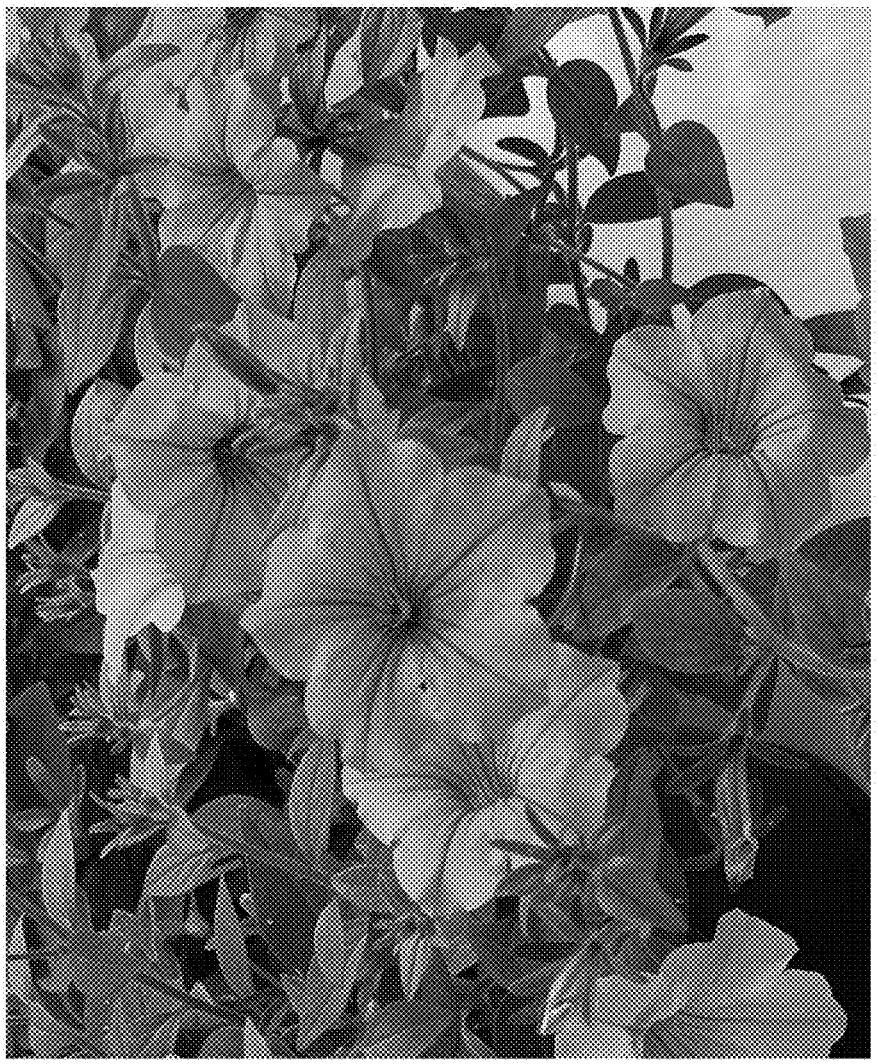

The photograph on the second sheet (FIG. 2) is a close-up view of a typical flowering plant of 'WNPETSVBG27'.

DETAILED BOTANICAL DESCRIPTION

The aforementioned photographs and following observations and measurements describe plants grown during the late spring and summer in 2.5-quart containers in a glass-covered greenhouse in Loudon, New Hampshire and under cultural practices typical of commercial *Petunia* production. During the production of the plants, day and night temperatures ranged from 21° C. to 29° C. and night temperatures ranged from 15° C. to 20° C. Plants were ten weeks from planting three-week old rooted young plants when the photographs were taken and were twelve weeks from planting when the detailed description was taken. Plants were pinched one time at the time of planting. In the following description, color references are made to The Royal Horticultural Society Colour Chart, 2015 Edition, except where general terms of ordinary dictionary significance are used.

Botanical classification: *Petunia* X *hybrida* 'WNPETSVBG27'.

Parentage: Naturally-occurring whole plant mutation of *Petunia* X *hybrida* 'USTUNI6001', disclosed in U.S. Plant Pat. No. 17,730.

Propagation:

*Type*.—Terminal vegetative cuttings.

*Time to initiate roots, summer*.—About three to four days at day temperatures about 29° C. and night temperatures about 17° C.

*Time to initiate roots, winter*.—About five to seven days at day temperatures about 21° C. and night temperatures about 17° C.

*Time to produce a rooted young plant, summer*.—About three weeks at day temperatures about 29° C. and night temperatures about 17° C.

*Time to produce a rooted young plant, winter*.—About four weeks at day temperatures about 21° C. and night temperatures about 17° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding plant habit to eventually spreading to trailing with subsequent development; freely branching habit with about seven to ten primary lateral branches with secondary laterals developing potentially at every node, dense and bushy plant form; pinching enhances development of lateral branches; vigorous growth habit and rapid growth rate.

*Plant height*.—About 17 cm to 20 cm.

*Plant diameter* (*area of spread*).—About 52 cm to 55 cm.

*Lateral branches*.—Length: About 45 cm to 48 cm. Diameter: About 3 mm to 4 mm. Internode length: About 2.5 cm. Strength: Strong; flexible, not brittle. Aspect: Initially upright to eventually outwardly spreading to trailing. Texture and luster: Densely pubescent; pubescence, fine; slightly glossy. Color, developing and developed: Close to 144A.

Leaf description:

*Arrangement*.—Alternate before flowering; opposite after flowers develop; leaves simple.

*Length, largest leaves*.—About 4.5 cm to 5 cm.

*Width, largest leaves*.—About 3 cm to 3.4 cm.

*Shape*.—Broadly ovate.

*Apex*.—Acute.

*Base*.—Obtuse.

*Margin*.—Entire, not undulate.

*Texture and luster, upper and lower surfaces*.—Sparsely pubescent, pubescence, minute; slightly glossy.

*Venation pattern*.—Pinnate, arcuate.

*Color*.—Developing and fully developed leaves, upper surface: Close to 146A; venation, close to 146B. Developing and fully developed leaves, lower surface: Close to 146B; venation, close to 146B to 146C.

*Petioles*.—Length: About 1.1 cm to 1.2 cm. Diameter: About 1.5 mm. Strength: Strong, flexible. Texture and luster, upper and lower surfaces: Moderately pubescent; semi-glossy. Color, upper surface: Close to 146B. Color, lower surface: Close to between 146B and 146C.

Flower description:

*Flower type and flowering habit*.—Single terminal and axillary salverform flowers; flowers face mostly upward to outwardly; freely flowering habit with flowers developing potentially at every node.

*Natural flowering season*.—Long day responsive; long flowering period, plants flower from early spring until frost in the autumn, flowering continuous during this period; early flowering habit, depending on temperature, plants begin flowering about 27 days after planting/pinching rooted young plants.

*Flower longevity on the plant*.—Depending on temperature, individual flowers last about five to seven days; petals not persistent, and sepals, persistent.

*Fragrance*.—None detected.

*Flower buds, just before petals part*.—Length: About 3.2 cm. Diameter: About 5 mm. Shape: Oblong, elongate. Texture and luster: Pubescent; slightly glossy to matte. Color, immature sepals, lower surface: Close to 146A Color, immature petals, lower surface: Proximally, close to between 144A and 146A; distally, close to 76A.

*Flower diameter*.—About 4.7 cm to 5.1 cm.

*Flower depth* (*height*).—About 3 cm to 3.3 cm.

*Throat diameter*.—About 7.5 mm.

*Tube length*.—About 2.4 cm to 2.6 cm.

*Tube diameter, distally*.—About 8 mm to 8.5 mm.

*Tube diameter, proximally*.—About 1.5 mm to 2 mm.

*Petals*.—Quantity and arrangement: Five petals fused in a single salverform whorl. Petal lobe length (from throat): About 2.1 cm to 2.5 cm. Petal lobe width: About 2.2 cm to 2.4 cm. Petal lobe shape: Roughly spatulate. Petal lobe apex: Cuspidate. Petal lobe margin: Entire; slightly undulate. Petal lobe texture and luster, upper surface: Smooth, glabrous; velvety; matte. Petal lobe texture and luster, lower surface: Slightly pubescent; matte. Throat texture and luster: Smooth, glabrous; matte. Tube texture and luster: Moderately pubescent; matte. Color: When opening, upper surface: Close to 68A. When opening, lower surface: Close to 77C. Fully opened, upper surface: Close to 68A; midvein, close to 67A and secondary venation, close to 68A; becoming closer to 68B with subsequent development, Fully opened, lower surface: Close to N74D; venation, close to 144A to 144B; color becoming closer to 75B with subsequent development. Flower throat (inside): Close to 68B; venation, close to 67A. Flower tube (outside): Close to N74D; venation, close to 144A to 144B.

*Sepals*.—Quantity and arrangement: Typically five sepals fused towards the base in a single star-shaped whorl; sepals flaring and arching outwardly. Calyx length: About 5 mm. Calyx diameter: About 1.75 cm. Length: About 8.5 mm. Width: About 2.5 mm to 3 mm. Shape: Acicular. Apex: Acute. Margin: Entire. Texture and luster, upper surface: Sparsely to moderately pubescent; pubescence, fine; matte. Texture and luster, lower surface: Moderately pubescent; pubescence, fine; matte. Color, upper and lower surfaces: Close to 146A.

*Peduncles, terminal flowers*.—Length: About 2.75 cm to 3 cm. Width: About 1 mm. Strength: Moderately strong to strong; wiry and flexible, not brittle. Angle: About 40° to 45° from the stem axis. Texture and luster: Moderately to densely pubescent; matte to slightly glossy. Color: Close to 146A.

*Reproductive organs*.—Stamens: Quantity per flower: Typically, five. Filament length: About 2.25 cm. Filament color: Close to NN155D. Anther length: About 1 mm. Anther shape: Bi-lobed. Anther color: Close to 158C. Pollen amount: None observed. Pistils: Quantity per flower: One. Pistil length: About 2.4 cm to 2.5 cm. Style length: About 2.1 cm to 2.2 cm. Style color: Close to 154D; distally, tinged with close to N77A. Stigma diameter: About 1.5 mm. Stigma shape: Rounded. Stigma color: Close to NN77A. Ovary color: Close to 144A.

*Seeds and fruits*.—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have good garden performance and have been observed to tolerate rain, wind, high light conditions and temperatures ranging from about 4° C. to about 40° C.

It is claimed:

1. A new and distinct *Petunia* plant named 'WNPETSVBG27' as herein illustrated and described.

* * * * *